United States Patent
Chuang

(10) Patent No.: US 8,447,391 B2
(45) Date of Patent: May 21, 2013

(54) DETECTION METHOD FOR DETECTING QRS WAVE

(75) Inventor: Chun-Te Chuang, Kaohsiung (TW)

(73) Assignee: Industrial Technology Research Institute (TW)

(*) Notice: Subject to any disclaimer, the term of this patent is extended or adjusted under 35 U.S.C. 154(b) by 586 days.

(21) Appl. No.: 12/477,860

(22) Filed: Jun. 3, 2009

(65) Prior Publication Data

US 2010/0168594 A1 Jul. 1, 2010

(30) Foreign Application Priority Data

Dec. 26, 2008 (TW) ............................ 97150827 A

(51) Int. Cl.
*A61B 5/04* (2006.01)
*A61N 1/00* (2006.01)

(52) U.S. Cl.
USPC ............... 600/521; 607/33; 607/54; 607/61; 607/136

(58) Field of Classification Search ..... 600/521; 607/33, 607/54, 61, 136
See application file for complete search history.

(56) References Cited

U.S. PATENT DOCUMENTS

| | | | |
|---|---|---|---|
| 4,240,442 A | 12/1980 | Andresen et al. | |
| 4,250,889 A * | 2/1981 | Levin | 600/521 |
| 4,796,638 A * | 1/1989 | Sasaki | 600/509 |
| 5,025,794 A | 6/1991 | Albert et al. | |
| 5,048,535 A | 9/1991 | Maruyama | |
| 5,702,425 A * | 12/1997 | Wickham | 607/9 |
| 5,758,654 A | 6/1998 | Burton-Krahn et al. | |
| 5,779,645 A * | 7/1998 | Olson et al. | 600/518 |
| 5,827,195 A | 10/1998 | Lander | |
| 5,947,909 A | 9/1999 | Watrous | |
| 6,625,484 B2 | 9/2003 | Kohler et al. | |
| 6,937,888 B2 | 8/2005 | Kohler et al. | |
| 7,254,439 B2 | 8/2007 | Misczynski et al. | |
| 7,289,844 B2 | 10/2007 | Misczynski et al. | |
| 2006/0116595 A1 * | 6/2006 | Palreddy et al. | 600/516 |

FOREIGN PATENT DOCUMENTS

| | | |
|---|---|---|
| TW | 167414 | 9/1991 |
| TW | 0033445 | 6/1998 |
| TW | 200738214 | 10/2007 |

OTHER PUBLICATIONS

Office Action dated Nov. 9, 2011 from corresponding application TW 097150827.

* cited by examiner

*Primary Examiner* — Nicole F Lavert
(74) *Attorney, Agent, or Firm* — Lowe Hauptman Ham & Berner, LLP

(57) ABSTRACT

A detection method for detecting a QRS wave is disclosed. An electrocardiogram (ECG) signal is provided. The ECG signal is enhanced to generate a processed signal. A first crest of the processed signal is determined. Each crest following the first crest is defined as a second crest. The level of each second crest is higher than a first threshold value. The result of defining the second crest is utilized to determine whether the QRS wave has occurred and approached a first crest.

17 Claims, 10 Drawing Sheets

DETECTION METHOD FOR DETECTING QRS WAVE

CROSS REFERENCE TO RELATED APPLICATIONS

This Application claims priority of Taiwan Patent Application No. 097150827, filed on Dec. 26, 2008, the entirety of which is incorporated by reference herein.

BACKGROUND

1. Technical Field

The disclosure relates to a detection method, and more particularly to a detection method for detecting a QRS wave.

2. Description of the Related Art

An electrocardiogram (ECG) signal is an important indicator for determining cardiovascular diseases. The rate or gap between heartbeats can be determined according to a QRS wave of the ECG signal. FIG. 1 is a schematic diagram of a normal ECG signal. The ECG signal comprises a P wave, a QRS wave, and a T wave. The P wave, the QRS wave, and the T wave are sequentially generated. The P wave occurs in the region 110. The QRS wave occurs in the region 120. The T wave occurs in the region 130. As shown in FIG. 1, the QRS wave in the region 120 is obvious.

However, the QRS wave in the region 120 may be unobvious during some cases. FIGS. 2a and 2b are schematic diagrams of abnormal ECG signals. As shown in FIG. 2a, the QRS wave is mixed with the former one. Referring to FIG. 2b, the QRS wave is opposite to the normal QRS wave. Accordingly, the rate or gap between heartbeats cannot be normally determined according to the abnormal QRS wave shown in FIG. 2a or 2b.

BRIEF SUMMARY

A detection method for detecting a QRS wave is provided. An exemplary embodiment of a detection method of the disclosure is described in the following. An electrocardiogram (ECG) signal is provided. The ECG signal is enhanced to generate a processed signal. In the step of enhancing the ECG signal to generate the processed signal, a filter is utilized to filter the ECG signal, a mask method is utilized to process the filtered ECG signal, and the masked ECG signal is normalized. A first crest of the processed signal is detected by using the first threshold value. A time period following the first crest is defined. Each crest following the first crest is detected by using the first threshold value within the time period. Each detected crest following the first crest is defined as a second crest when the detected crest following the first crest is higher than the first threshold value. It is determined whether the QRS wave is adjacent to the first crest according to the detecting results of the first crest and the second crests.

A detailed description is given in the following embodiments with reference to the accompanying drawings.

BRIEF DESCRIPTION OF THE DRAWINGS

The disclosure can be more fully understood by referring to the following detailed description and examples with references made to the accompanying drawings, wherein.

DETAILED DESCRIPTION

The following description is of carrying out the disclosure. This description is made for the purpose of illustrating the general principles of the disclosure and should not be taken in a limiting sense. The scope of the disclosure is best determined by reference to the appended claims.

Figure 1:
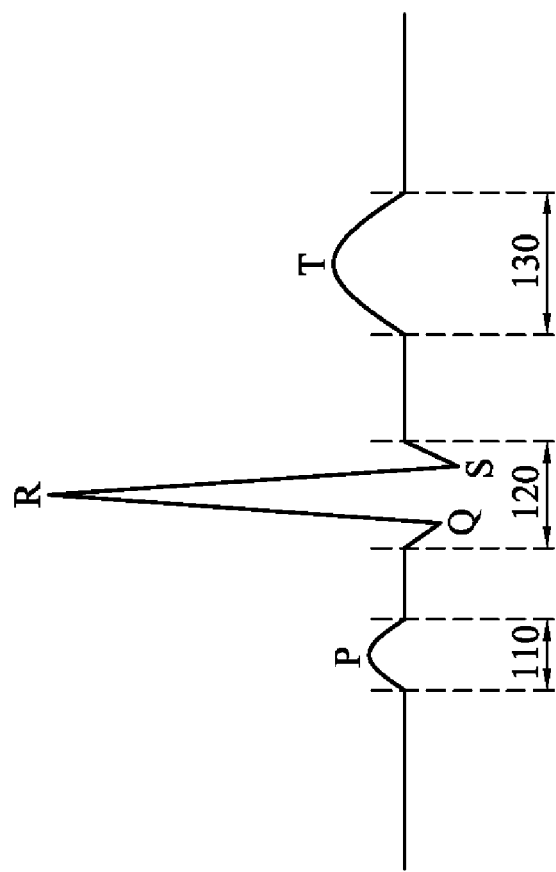
FIG. 1 is a schematic diagram of a normal ECG signal.
Figure 2A:
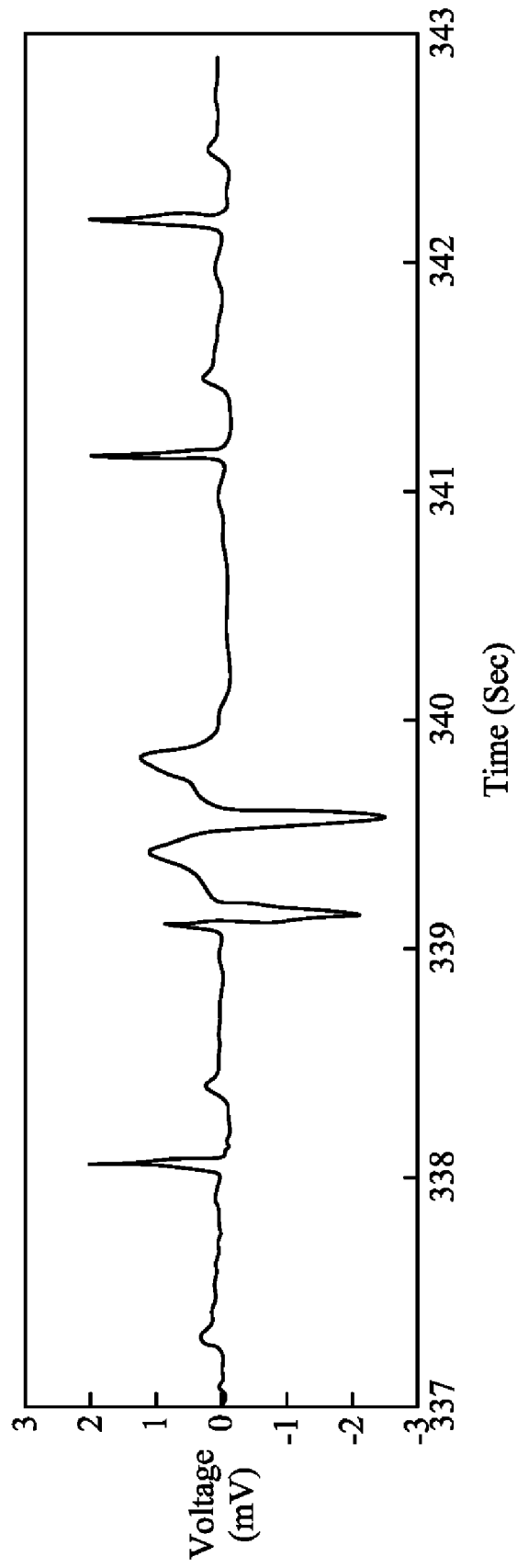
FIGS. 2a and 2b are schematic diagrams of abnormal ECG signals.
Figure 2B:
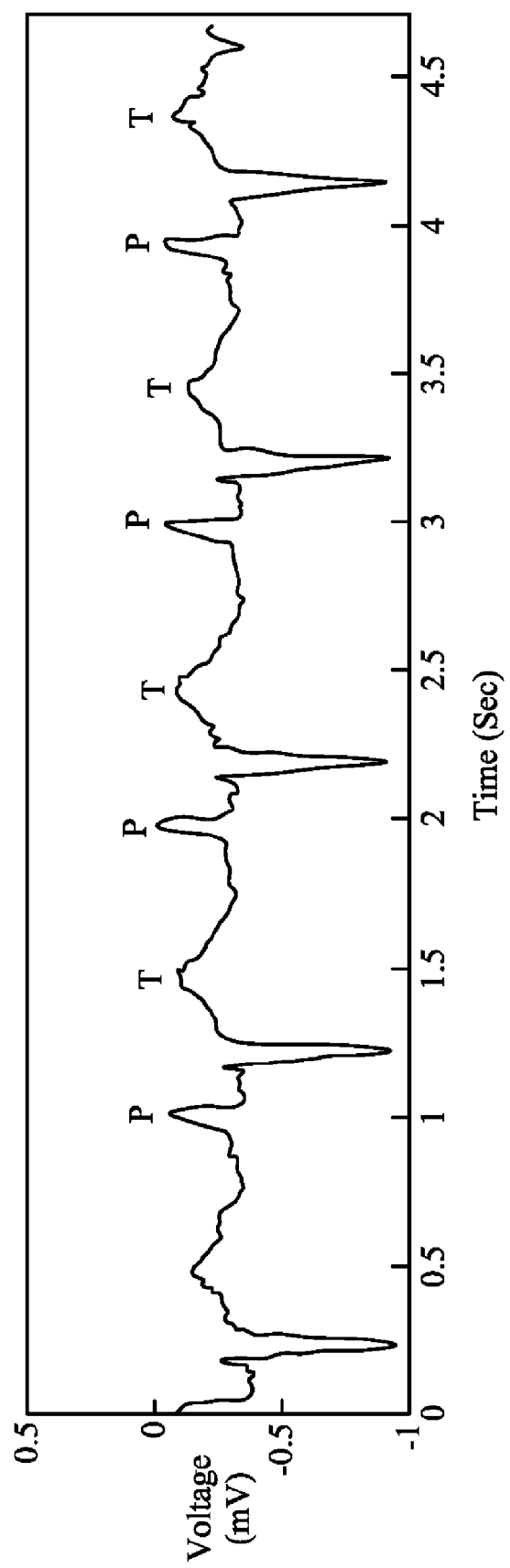
Figure 3A:
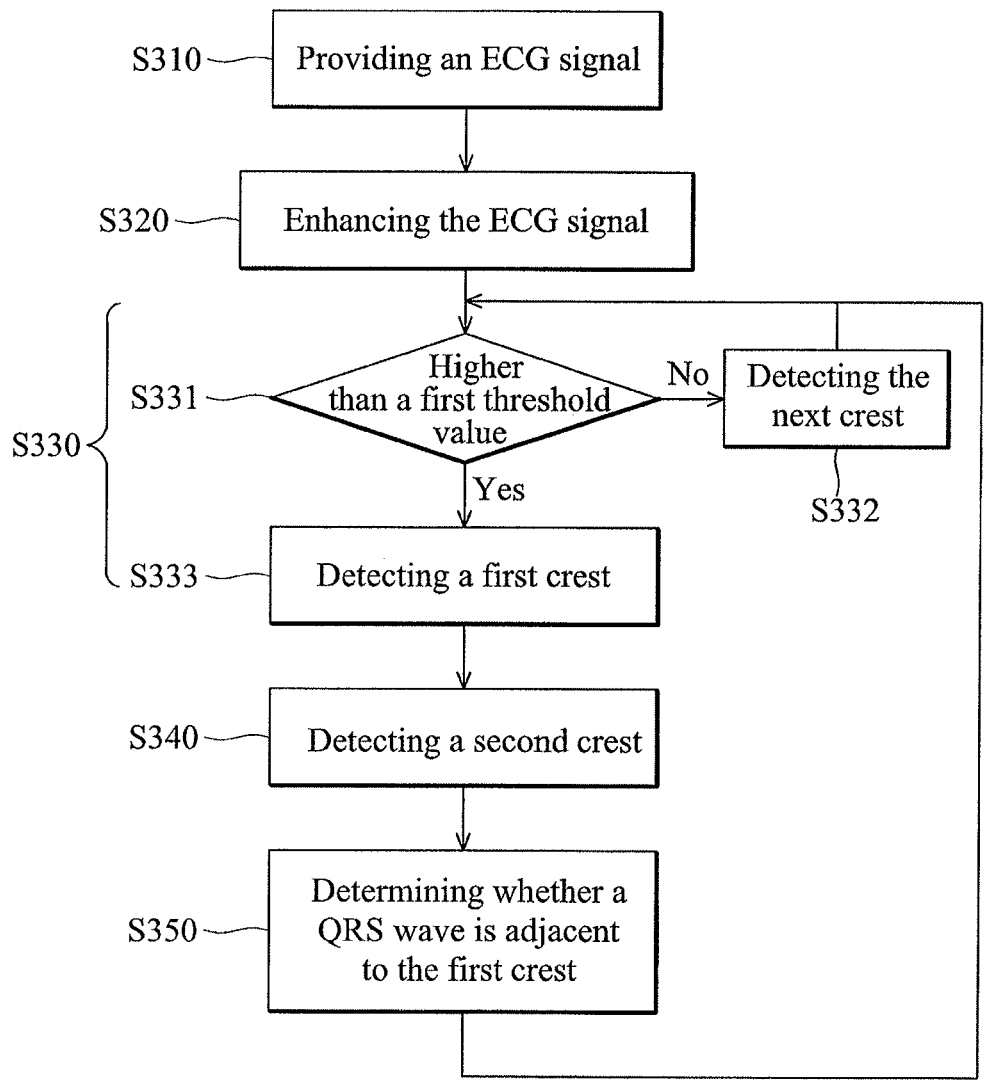
FIG. 3a is a flowchart of an exemplary embodiment of a detection method.

FIG. 3a is a flowchart of an exemplary embodiment of a detection method. First, an ECG signal is provided (step S310). The ECG signal may be an abnormal ECG signal as shown in FIG. 2a or 2b.

Figure 4A:
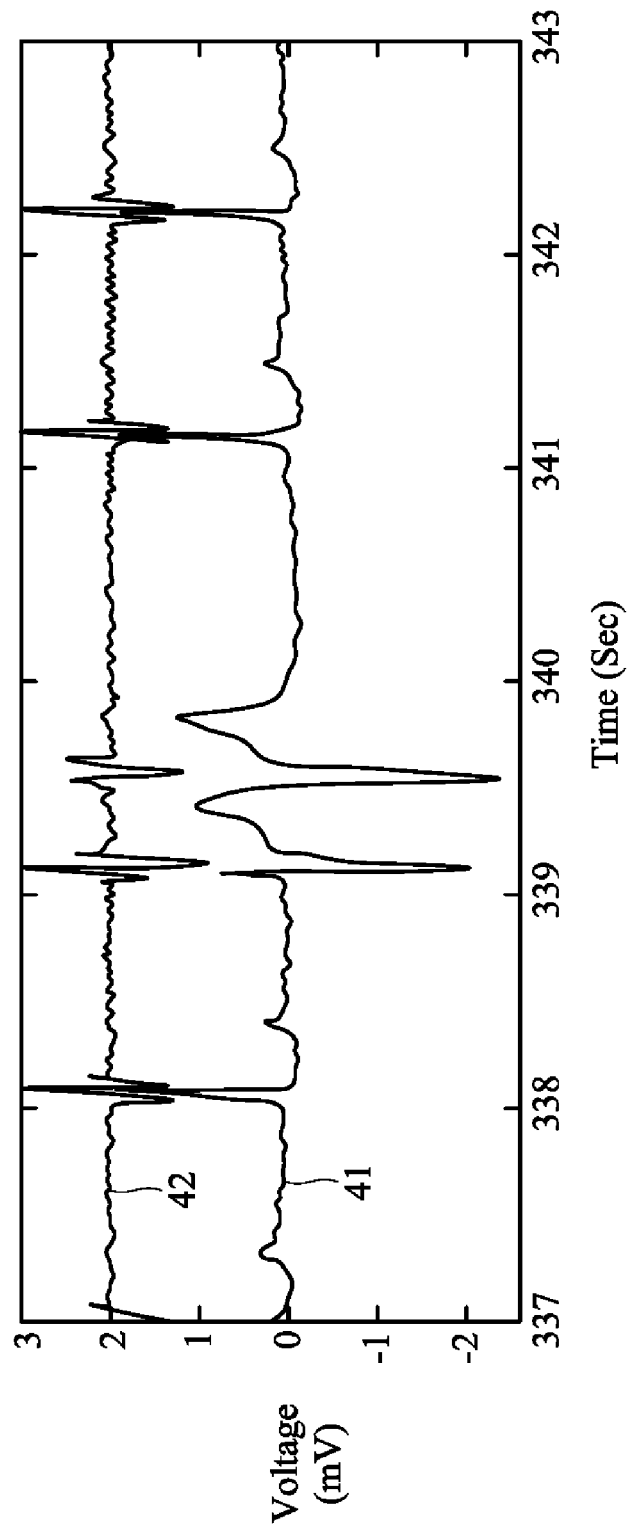
FIGS. 4a and 4b show exemplary embodiments of a processed signal.
Figure 4B:
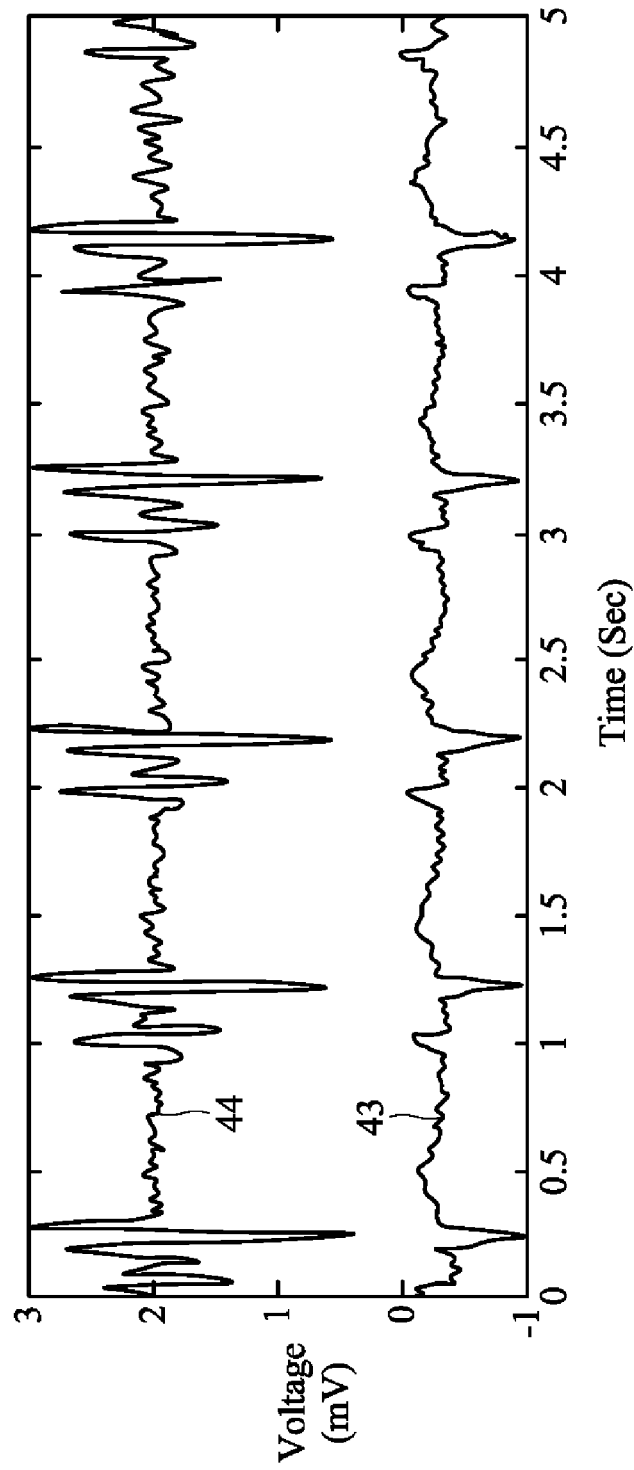

The ECG signal is enhanced to generate a processed signal (step S320). FIGS. 4a and 4b show exemplary embodiments of the enhanced ECG signal (i.e. the processed signal). Referring to FIG. 4a, the curve 41 is an abnormal ECG signal, which is the same as the curve shown in FIG. 2a. When the curve 41 is enhanced, the enhanced result is shown as the curve 42. The curve 42 represents the enhanced ECG signal. Referring to FIG. 4b, the curve 43 is an abnormal ECG signal, which is the same as the curve shown in FIG. 2b. When the curve 43 is enhanced, the enhanced result is shown as the curve 44. The curve 44 represents the enhanced ECG signal. The curves 42 and 44 serve as the processed signals described in the step S320.

A first crest of the processed signal is detected (step S330). In this embodiment, when a crest exceeds a first threshold value, the crest is defined as a first crest. Thus, the crest of the processed signal is compared with the first threshold value (step S331). If the crest of the processed signal is lower than the first threshold value, the next crest of the processed signal is compared with the first threshold value (step S332). If the crest of the processed signal is higher than the first threshold value, the crest higher than the first threshold value is defined as a first crest (step S333). In other embodiments, the first crest may be lower than the first threshold value. For example, any crest of the processed signal can be directly defined as a first crest.

Each crest following the first crest is defined as a second crest (step S340). In this embodiment, the first and the second crests are higher than the first threshold value, but the disclosure is not limited thereto. In another embodiment, the first and the second crests are lower than the first threshold value. In other embodiments, one of the first and the second crest is lower than the first threshold value.

The QRS wave is determined to have occurred adjacent to the first crest according to the result of detecting the second crest (step S350). For example, the QRS wave is determined according to the number, the amplitudes, or the positions of the second crests.

In one embodiment, after detecting the first crest, counting is executed for determining the number of the second crests during a timing period. For example, when the first crest is detecting, the number of the second crests is counted during a timing period (e.g. 300 ms). Thus, it is determined that a QRS wave is adjacent to the first crest according to the number of the second crests.

Figure 3B:
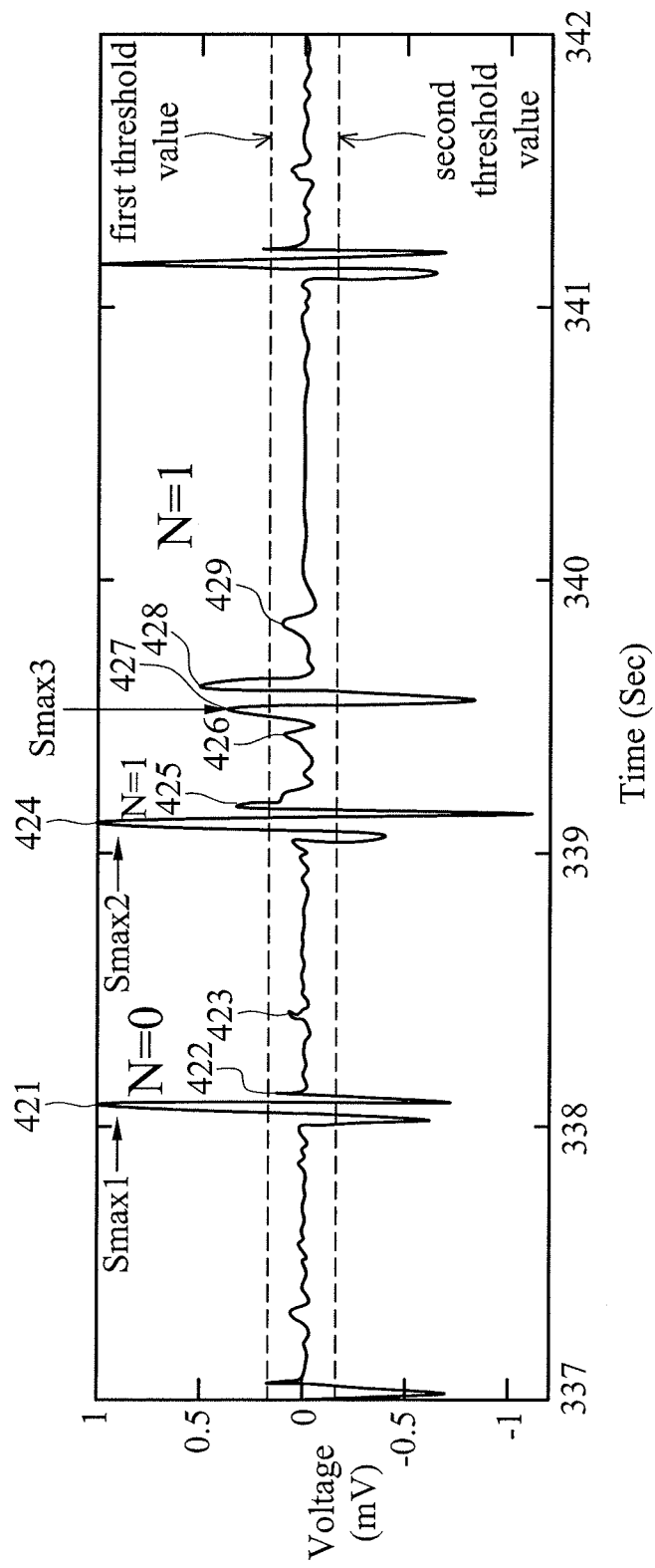
FIG. 3b is a schematic diagram of an ECG signal.

In this embodiment, when the step S350 is executed, then the step S330 is executed to detect the next first crest. The gap between the QRS waves is determined when the steps S330 to S350 are repeated. Referring to FIG. 3b, FIG. 3b is a schematic diagram of an ECG signal. The curve shown in FIG. 3b is the same as the curve 42 shown in FIG. 4a and is an transformed ECG signal (i.e. the processed signal). The symbol N represents the number of second crests.

Since the crest 421 of the processing signal is higher than the first threshold value, the crest 421 is defined as a first crest Smax1. As shown in FIG. 3b, the crests 422 and 423 following the crest 421 are not higher than the first threshold value during a timing period. Thus, the number N of second crests following the crest 421 is equal to 0, which represents that a QRS wave is adjacent to the first crest Smax 1.

Assuming that the first crest is required to be higher than the first threshold value, since the crests 422 and 423 of the processed signal are lower than the first threshold value, each of the crests 422 and 423 cannot be defined as a first crest.

Since the crest 424 of the processed signal is higher than the first threshold value, the crest 424 can be defined as another first crest Smax2. During a timing period following the crest 424, the crest 425 is higher than the first threshold value. Thus, the crest 425 is defined as a second crest. Since the crest 426 is lower than the first threshold value, the crest 426 cannot be defined as a second crest. Since the number N of second crests following the first crest Smax2 equal to 1, it represents that a QRS wave is adjacent to the first crest Smax2.

Similarly, since the crest 427 of the processed signal is higher than the first threshold value, the crest 427 is defined as a first crest Smax3. During a timing period following the crest 427, the crest 428 is higher than the first threshold value. Thus, the crest 428 is defined as a second crest. Since the crest 429 is lower than the first threshold value, the crest 429 cannot be defined as a second crest. Since the number N of second crests following the first crest Smax3 is equal 1, it represents that a QRS wave is adjacent to the first crest Smax3.

In this embodiment, the first crests Smax1~Smax3 are not only higher than the first threshold value (e.g. 0.2), but also higher than a third threshold value (e.g. 0.6), but the disclosure is not limited thereto. In some embodiments, the first crests Smax1~Smax3 may be lower than the first threshold value.

Figure 5A:
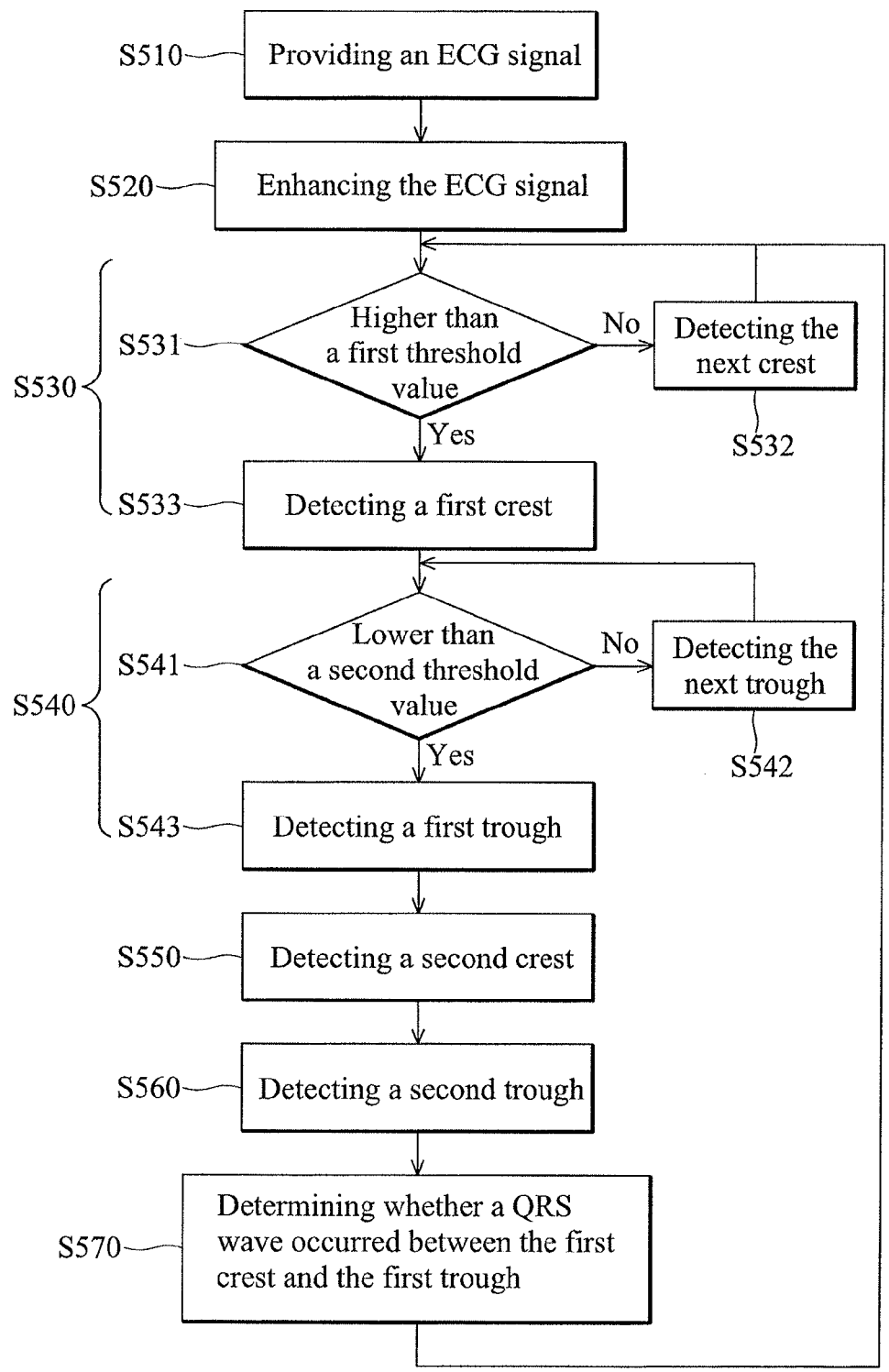
FIG. 5a is a flowchart of another exemplary embodiment of the detection method.

FIG. 5a is a flowchart of another exemplary embodiment of the detection method. FIG. 5a is similar to FIG. 3a except for the addition of steps S540 and S560. Since the steps S510-530 and S550 are similar to the steps S310-S330 and S340, descriptions of the steps S510-530 and S550 are omitted. As shown in FIG. 5a, after the step S530, a first trough is detected (step S540). In this embodiment, the first trough is required to be lower than a second threshold value. To satisfy the criterion, a trough of the processed signal is compared with the second threshold value (step S541). If the trough of the processed signal is not lower than the second threshold value, the next trough of the processed signal is compared with the second threshold value (step S542). If the trough of the processed signal is lower than the second threshold value, the trough is defined as a first trough (step S543).

When the second crest is detected, each trough following the first trough is defined as a second trough (step S560). In this embodiment, the second trough is lower than the second threshold value. Accordingly, a QRS wave is determined to have occurred between the first crest and the first trough according to the second crest and the second trough (step S570). In some embodiments, it is determined that a QRS wave has occurred between the first crest and the first trough according to the numbers, the amplitudes, or the positions of the second crest and the second trough.

Figure 5B:
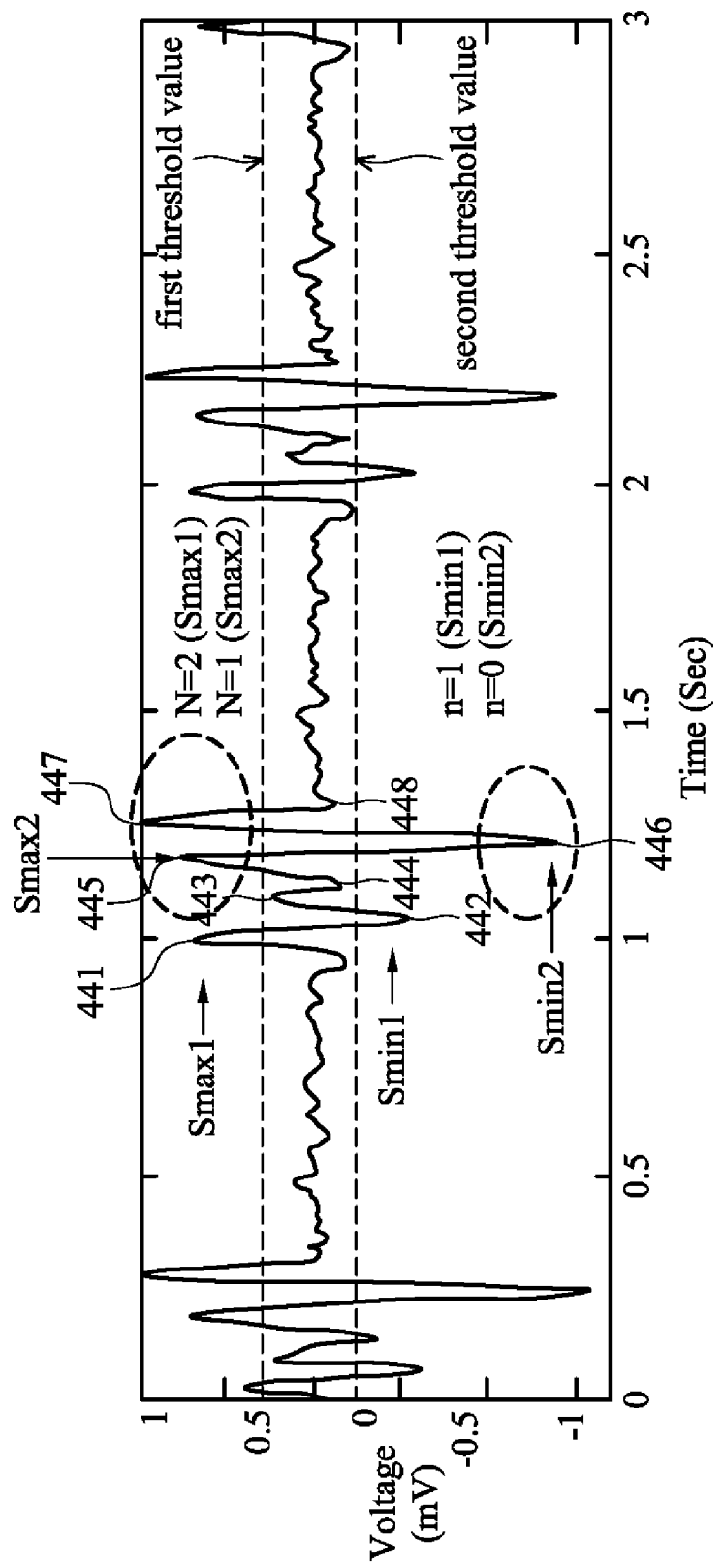
FIG. 5b is a schematic diagram of an ECG signal.

FIG. 5b is a schematic diagram of an ECG signal. The curve shown in FIG. 5b is the same as the curve 44 shown in FIG. 4b and is an enhanced ECG signal (i.e. the processed signal). The symbol N represents the number of second crests. The symbol n represents the number of second troughs.

Since the crest 441 of the processed signal is higher than a first threshold value, the crest 441 is defined as a first crest Smax1. In addition, the trough 442 of the processed signal is lower than a second threshold value. Accordingly, the trough 442 is defined as a first trough Smin1. In this embodiment, the first trough is detected after detecting the first crest.

As shown in FIG. 5b, the crests 445 and 447 are higher than the first threshold value during a timing period following the first crest Smax1. Thus, the crest 445 is defined as a second crest and the crest 447 is defined as another second crest. Since the crest 443 is lower than the first threshold value, the crest 443 cannot be defined as a second crest. Accordingly, the number N of second crests following the first crest Smax1 is equal to 2, which represents that the wave between the first crest Smax1 and the first trough Smin1 is not a QRS wave. In some embodiments, when the wave between the first crest Smax1 and the first trough Smin1 is not a QRS wave, the number N of second crests following the first crest Smax1 may exceed 2.

Additionally, the trough 446 is lower than the second threshold value and the troughs 444 and 448 are not lower than the second threshold value. Thus, the trough 446 is defined as a second trough and each of the troughs 444 and 448 cannot be defined as another second trough. Therefore, the number n of second troughs following the first trough Smin1 is equal to 1, which represents that the wave between the first crest Smax1 and the first trough Smin1 may not be a QRS wave. In other embodiments, the number N of second crests following the first crest Smax1 may be equal to or exceed 2, which represents that the occurrence adjacent to the first crest is noise. Thus, the occurrence between the first crest and the first trough can be determined according to the number n of second troughs.

The crests following the first crest Smax1 are continuously determined whether they may be detected and defined as a first crest. In this embodiment, the crest of the processed signal is defined as the first crest when the crest is higher than the first threshold value. Thus, the crest 443 is not defined as a first crest. Since the crest 445 is higher than the first threshold value, the crest 445 is defined as a first crest Smax2. After the first crest Smax2, since the trough 446 is lower than the second threshold value, the trough 446 is defined as a first trough Smin2.

After the first crest Smax2, since the crest 447 is higher than the first threshold value, the crest 447 is defined as a second crest. Thus, the number N of second crests following the first crest Smax2 is equal to 1, which represents that a QRS wave has occurred between the first crest Smax2 and the first trough Smin2. In addition, after the first trough Smin2, the processed signal does not comprise a trough, which is lower than the second threshold value. Thus, the number n of second troughs is equal to 0. Since the number N of second crests is equal to 1, when the number n of second troughs is equal to 0, it is further determined that a QRS wave has occurred between the first crest Smax2 and the first trough Smin2.

Furthermore, if the numbers of the second crests and second troughs are equal to 0, it represents that a QRS wave has not occurred between the first crest and the first trough. If the first crest is higher than the third threshold value, it represents that a QRS wave is adjacent to the first crest even if the numbers of the second crest and second troughs are equal to 0.

Figure 6:
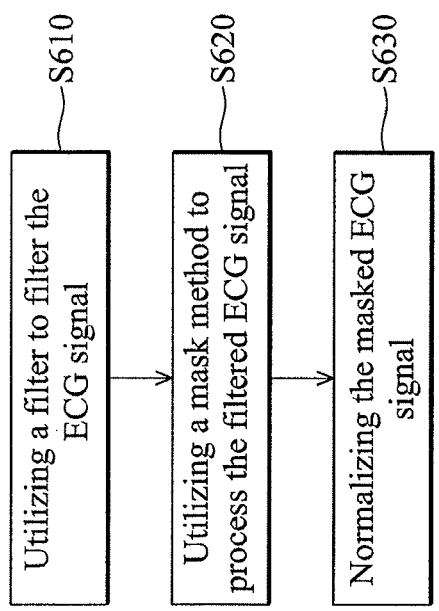
FIG. 6 is an exemplary embodiment of a transforming step.

FIG. 6 is an exemplary embodiment of an enhancing step (e.g. the step S320 or S520). A filter is utilized to process the ECG signal (step S610). In one embodiment, a low-pass filter or a band-pass filter can be utilized to process the ECG signal. Additionally, in this embodiment, the pass frequency is 0 to 5 Hz and the cut-off frequency is 12 to 18 Hz.

A mask method is utilized to process the filtered ECG signal (step S620). Thus, the QRS wave of the ECG signal is enhanced and the P wave and the T wave of the ECG signal are restrained. The mask method can be a 3-order or higher than 3-order method. For symmetry, the number of the order is odd. If the mask method is a 3-order method, the parameters can be [−1 2 −1] or [−1 0 1]. If the mask method is a 5-order method, the parameters can be [−1 −1 4 −1 −1] or [−2 −1 0 1 2].

In the step S620, the mask method executes a point change or a slope change for the filtered ECG signal. For a p-order mask, since p is odd, p=2k+1. In one embodiment, the mask method is a point enhanced method. In another embodiment, the mask method is a gradient enhanced method for processing the filtered ECG signal.

The point enhanced method is expressed by the following equation:

$$\begin{cases} M(n) = -1, n = 0 \sim k-1 \\ M(n) = 2*k, n = k \\ M(n) = -1, n = k+1 \sim 2k \end{cases}$$

, wherein the M is a mask, and k relates to p (p=2k+1).

The gradient enhanced method is expressed by the following equation:

$$M(n) = -k+n, n = 0 \sim 2k.$$

The masked ECG signal is next normalized (step S630). In one embodiment, the maximum of the signal is equal to 1 after normalization. Thus, the QRS wave is highlighted. For example, assuming that the original ECG signal is the same as the curve 41 as shown in FIG. 4a. After the step S610~630, a processed signal is generated and is the same as the curve 42, wherein the mask method is the point enhanced method. In another embodiment, assuming that the original ECG signal is the same as the curve 43 as shown in FIG. 4b. After the step S610~630, the processed signal is generated and is the same as the curve 44, wherein the mask method is the gradient enhanced method.

Since the QRS wave of the ECG signal may be unobvious, the enhancing steps are utilized to obtain an enhanced ECG signal (i.e. the processed signal). The first crest of the processed signal is determined to obtain the position of the QRS wave. The QRS wave is determined whether to have occurred and have approached a first crest according to the number of second crests following the first crest, or the amplitude or the position of the second crests following the first crest.

In some embodiments, the first trough of the processed signal is determined. Noise is determined whether to have occurred adjacent to the first crest according to the number, the amplitudes, or the positions of the second crests following the first trough. In addition, the QRS wave is determined to whether have occurred between the first crest and the first trough according to the number, the amplitudes, or the positions of the second troughs following the first trough.

While the disclosure has been described by way of example and in terms of the exemplary embodiments, it is to be understood that the disclosure is not limited to the presented embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A detection method for detecting a QRS wave, comprising:
    providing an electrocardiogram (ECG) signal;
    enhancing the ECG signal to generate a processed signal, wherein the step of enhancing the ECG signal to generate the processed signal comprises:
        utilizing a filter to filter the ECG signal to generate a filtered ECG signal;
        utilizing a mask method to process the filtered ECG signal to generate a masked ECG signal; and
        normalizing the masked ECG signal;
    defining a first threshold value;
    detecting a first crest of the processed signal by using the first threshold value;
    defining a time period following the first crest;
    detecting each crest following the first crest by using the first threshold value within the time period, wherein each detected crest following the first crest is defined as a second crest when the detected crest following the first crest is higher than the first threshold value; and
    determining whether the QRS wave occurs between the first crest and a first trough according to the detecting results of the first crest and the second crests.

2. The detection method as claimed in claim 1, wherein the step of determining whether the QRS wave occurs between the first crest and the first trough according to the detecting results of the first crest and the second crests comprises:
    detecting the number, the amplitudes, or the positions of the second crests within the time period following the first crest; and
    determining whether the QRS wave occurs between the first crest and the first trough according to the number, the amplitudes, or the positions of the second crests.

3. The detection method as claimed in claim 1, wherein the step of detecting the first crest of the processed signal by using the first threshold value comprises:
    comparing the first threshold value with a crest of the processed signal; and
    identifying the crest higher than the first threshold value as the first crest.

4. The detection method as claimed in claim 1, wherein the step of determining whether the QRS wave occurs between the first crest and the first trough according to the detecting results of the first crest and the second crests comprises:
    detecting a number of the second crests within the timing period following the first crest; and
    determining that the QRS wave occurs between the first crest and the first trough when the number of the second crests is equal to 0 or 1.

5. The detection method as claimed in claim 1, wherein the step of determining whether the QRS wave occurs between the first crest and the first trough according to the detecting results of the first crest and the second crests comprises:
    detecting a number of the second crests within the timing period following the first crest; and
    determining that the QRS wave does not occur between the first crest and the first trough when the number of the second crests is higher than 2 or is equal to 2.

6. The detection method as claimed in claim 1, wherein the filter filtering the ECG signal is a low-pass filter or a band-pass filter.

7. The detection method as claimed in claim 1, wherein the mask method processing the filtered ECG signal is a point enhanced method or a gradient enhanced method.

8. A detection method for detecting a QRS wave, comprising:
provided an electrocardiogram (ECG) signal;
enhancing the ECG signal to generate a processed signal, wherein the step of enhancing the ECG signal to generate the processed signal comprises:
utilizing a filter to filter the ECG signal to generate a filtered ECG signal;
utilizing a mask method to process the filtered ECG signal to generate a marked ECG signal; and
normalizing the masked ECG signal;
defining a first threshold value;
detecting a first crest of the processed signal by using the first threshold value;
defining a time period following the first crest;
detecting each crests following the first crest by using the first threshold value within the time period, wherein each detected crest following the first crest is defined as a second crest when the detected crest following the first crest is higher than the first threshold value;
defining a second threshold value;
detecting a first trough of the processed signal by using the second threshold value, wherein the first trough follows the first crest;
detecting each trough following the first trough by using the second threshold value within the time period, wherein each detected trough following the first trough is defined as a second trough when the detected trough following the first trough is lower than the second threshold value; and
determining whether the QRS wave occurs between the first crest and the first trough according to the detecting results of detecting the first crest, the second crest, the first trough and the second trough.

9. The detection method as claimed in claim 8, wherein the step of detecting the first trough of the processed signal by using the second threshold value comprises:
comparing the second threshold value with a trough of the processed signal; and
identifying the trough lower than the second threshold value as the first trough,
wherein the step of detecting the second trough of the processed signal by using the second threshold value comprises:
comparing the second threshold value with a trough of the processed signal, following the first trough; and
identifying each trough following the first trough and lower than the second threshold value as the second trough.

10. The detection method as claimed in claim 8, wherein the step of determining whether the QRS wave occurs between the first crest and the first trough according to the detecting results of detecting the first crest, the second crest, the first trough and the second trough comprises:
detecting a number, or amplitudes or the positions of the second troughs within the time period following the first trough; and
determining whether the QRS wave occurs between the first crest and the first trough according to the number, or the amplitudes or the positions of the second troughs.

11. The detection method as claimed in claim 8, wherein the step of determining whether the QRS wave occurs between the first crest and the first trough according to the detecting results of detecting the first crest, the second crest, the first trough and the second trough comprises:
detecting a number of the second troughs within the time period following the first trough; and
determining that the QRS wave did not occur between the first crest and the first trough when the number of the second troughs is not equal to 0.

12. The detection method as claimed in claim 8, wherein the step of determining whether the QRS wave occurred between the first crest and the first trough according to the detecting results of detecting the first crest, the second crest, the first trough and the second trough comprises:
detecting a number of the second crests and second troughs; and
determining that the QRS wave occurs between the first crest and the first trough when the number of the second crest equals to 1 and the number of the second trough equals to 0.

13. The detection method as claimed in claim 8, wherein the step of determining whether the QRS wave occurs between the first crest and the first trough according to the detecting results of detecting the first crest, the second crest, the first trough and the second trough comprises:
detecting a number of the second crests and second troughs; and
determining that the QRS wave did not occur between the first crest and the first trough when the numbers of the second crests and second troughs are equal to 0.

14. The detection method as claimed in claim 8, further comprising:
comparing the level of the first crest with a third threshold value, wherein the third threshold value is higher than the first threshold value;
detecting a number of the second crests and second troughs; and
determining that the QRS wave occurs between the first crest and the first trough when the level of the first crest is higher than the third threshold value and the numbers of the second crests and second troughs are equal to 0.

15. The detection method as claimed in claim 8, wherein the step of determining whether the QRS wave occurs between the first crest and the first trough according to the detecting results of detecting the first crest, the second crest, the first trough and the second trough comprises:
detecting a number of the second crests and second troughs; and
determining that the QRS wave does not occur between the first crest and the first trough when the number of the second crest is higher than 2 or is equal to 2.

16. The detection method as claimed in claim 8, wherein the filter filtering the ECG signal is a low-pass filter or a band-pass filter.

17. The detection method as claimed in claim 8, wherein the mask method processing the filtered ECG signal is a point enhanced method or a gradient enhanced method.

* * * * *